US010410748B2

(12) United States Patent
Fitzgerald et al.

(10) Patent No.: US 10,410,748 B2
(45) Date of Patent: Sep. 10, 2019

(54) SYSTEM FOR PROVIDING AN OVERVIEW OF PATIENT MEDICAL CONDITION

(75) Inventors: Loretta A. Fitzgerald, Collegeville, PA (US); Vickilyn Spiotta, Shaker Heights, OH (US); Christian Lampone, Pipersville, PA (US)

(73) Assignee: CERNER INNOVATION, INC., Kansas City, KS (US)

( * ) Notice: Subject to any disclaimer, the term of this patent is extended or adjusted under 35 U.S.C. 154(b) by 1778 days.

(21) Appl. No.: 11/862,775

(22) Filed: Sep. 27, 2007

(65) Prior Publication Data

US 2009/0119128 A1 May 7, 2009

Related U.S. Application Data

(60) Provisional application No. 60/827,768, filed on Oct. 2, 2006.

(51) Int. Cl.
*G16H 50/20* (2018.01)
*G16H 40/63* (2018.01)
(Continued)

(52) U.S. Cl.
CPC .............. *G16H 50/20* (2018.01); *G06Q 50/22* (2013.01); *G06Q 50/24* (2013.01); *G16H 10/60* (2018.01); *G16H 40/63* (2018.01)

(58) Field of Classification Search
CPC ................................ G06Q 50/22; G06Q 50/24
(Continued)

(56) References Cited

U.S. PATENT DOCUMENTS 5,447,164 A 9/1995 Shaya et al.
5,508,912 A 4/1996 Schneiderman
(Continued)

FOREIGN PATENT DOCUMENTS

JP 2002268787 A 9/2002

OTHER PUBLICATIONS

Clinical Documentation: Care Management, Diagnosis NANDA, Patient Record, electronic Medical Record http://www.americanhealthnet.com/products/clinical-documentation.html.
(Continued)

*Primary Examiner* — Lena Najarian
(74) *Attorney, Agent, or Firm* — Shook, Hardy and Bacon LLP (57) ABSTRACT

A system provides an overview of patient medical condition identifying both long term and short term medical conditions. The system includes a designation processor for designating an identified patient medical condition as being long term in response to user command. At least one repository stores information associating a designated long term patient medical condition with a patient and with multiple encounter identifiers identifying corresponding interactions of the patient with a healthcare provider organization and medical conditions associated with the encounters. A user interface initiates generation of data representing a composite display image window including data identifying a designated long term patient medical condition together with encounters and medical conditions associated with the encounters providing a user an overview of long term and short term medical conditions of a patient.

11 Claims, 3 Drawing Sheets

(51) Int. Cl.
  *G16H 10/60* (2018.01)
  *G06Q 50/22* (2018.01)
  *G06Q 50/24* (2012.01)

(58) Field of Classification Search
  USPC .......................................... 705/2, 3; 600/300
  See application file for complete search history.

(56) References Cited

U.S. PATENT DOCUMENTS

| | | |
|---|---|---|
| 5,937,042 A | 9/1999 | Sofman |
| 6,002,398 A | 12/1999 | Wilson |
| 6,049,812 A | 4/2000 | Bertram et al. |
| 6,082,776 A * | 7/2000 | Feinberg ........................ 283/72 |
| 6,166,736 A | 12/2000 | Hugh |
| 6,288,753 B1 | 9/2001 | DeNicola et al. |
| 6,301,573 B1 | 10/2001 | McIlwaine et al. |
| 6,310,630 B1 | 10/2001 | Kulkami et al. |
| 6,359,634 B1 | 3/2002 | Cragun et al. |
| 6,370,355 B1 | 4/2002 | Ceretta et al. |
| 6,405,195 B1 | 6/2002 | Ahberg |
| 6,409,662 B1 | 6/2002 | Lloyd et al. |
| 6,542,910 B2 | 4/2003 | Cork et al. |
| 6,587,668 B1 | 7/2003 | Miller et al. |
| 6,628,311 B1 | 9/2003 | Fang |
| 2001/0020229 A1 | 9/2001 | Lash |
| 2002/0019749 A1* | 2/2002 | Becker .................. G06F 19/325 705/2 |
| 2002/0065686 A1 | 5/2002 | Monteleone et al. |
| 2002/0082870 A1 | 6/2002 | Penny et al. |
| 2002/0093537 A1 | 7/2002 | Bocioned et al. |
| 2002/0116221 A1 | 8/2002 | Fields et al. |
| 2002/0116226 A1 | 8/2002 | Auer et al. |
| 2003/0050800 A1 | 3/2003 | Brandt et al. |
| 2003/0060688 A1 | 3/2003 | Ciarniello et al. |
| 2003/0131026 A1 | 7/2003 | Cork et al. |
| 2003/0195774 A1* | 10/2003 | Abbo ................................ 705/3 |
| 2004/0024616 A1* | 2/2004 | Spector et al. ................... 705/2 |
| 2004/0034288 A1* | 2/2004 | Hennessy et al. ............ 600/300 |
| 2004/0199408 A1 | 10/2004 | Johnson |
| 2005/0015279 A1 | 1/2005 | Rucker |
| 2005/0108050 A1 | 5/2005 | Knapheide |
| 2005/0209891 A1 | 9/2005 | Jacobus et al. |
| 2006/0078867 A1 | 4/2006 | Penny et al. |
| 2006/0085223 A1 | 4/2006 | Anderson et al. |
| 2006/0106641 A1 | 5/2006 | Bartsch et al. |
| 2006/0242143 A1 | 10/2006 | Esham et al. |
| 2007/0162310 A1* | 7/2007 | Schmidt ........................... 705/3 |
| 2007/0192134 A1* | 8/2007 | Littenberg ............ G06F 19/345 705/2 |
| 2008/0004818 A1 | 1/2008 | Zaleski |
| 2008/0065422 A1 | 3/2008 | Weber |

OTHER PUBLICATIONS

NetCaptor Browser Tab Interface copyright 1998-2001 Stilesoft, Inc., website http://www.netcaptor.com, printed on Dec. 14, 2000.
"EarthNavigator" version 3.02, printed on Apr. 18, 2001, website http://www.earthnavigator.com/tour/tour2.htm, printed on Dec. 14, 2000.
NetCaptor 6.1.1 Final Available, printed on Dec. 14, 2000, website http://www.netcaptor.com.

* cited by examiner

SYSTEM FOR PROVIDING AN OVERVIEW OF PATIENT MEDICAL CONDITION

This is a non-provisional application of provisional application Ser. No. 60/827,768 filed Oct. 2, 2006, by L. A. Fitzgerald.

FIELD OF THE INVENTION

This invention concerns a system for providing an overview of patient medical condition identifying both long term and short term medical conditions and associated encounters (e.g., visits, treatment episodes).

BACKGROUND OF THE INVENTION

In known patient medical record management systems, a clinical diagnosis is added to a patient record, but in the record there is typically no association with a financial reimbursement related code diagnosis description, such as an ICD9 code. The financial diagnosis code is associated with a patient visit and needs to be re-entered when a patient continues with visits to treat medical conditions which continue with the patient for an extended duration such as over a patient lifetime. Such medical conditions include, diabetes, congestive heart failure, and cancer, for example. Known systems employ financial system paradigms, in which visit identifier, and clinical diagnosis and associated code are typically re-entered for each visit.

In known systems, a clinical diagnosis is re-entered into a patient medical record management system in association with a visit record in response to a financial system requirement. Such systems fail to automatically manage a diagnosis which persists for a patient lifetime and burdens a clinician with a requirement to repetitively re-enter a clinical diagnosis in association with a visit record. Known systems also fail to provide a bridge between a financial diagnosis and clinical diagnosis. For example, an ICD9 code 174.2 description is: Malignant neoplasm of female breast Upper-inner quadrant and a corresponding clinical description is Breast Cancer. Known systems fail to automatically link financial and clinical diagnoses for use in appropriate record maintenance. A system according to invention principles addresses these deficiencies and related problems.

SUMMARY OF THE INVENTION

A system automatically converts a financial diagnosis description of a medical condition, such as an ICD 9 code, into clinical terminology used by clinicians and associates a clinical diagnosis with a patient in a record that persists the association across multiple patient visits and not just for one visit. A system provides an overview of patient medical condition identifying both long term conditions (e.g., diabetes, congestive heart failure, and cancer) and short term medical conditions. The system includes a designation processor for designating an identified patient medical condition as being long term in response to user command. At least one repository stores information associating a designated long term patient medical condition with a patient and with a plurality of encounter identifiers identifying corresponding interactions of the patient with a healthcare provider organization and medical conditions associated with the encounters. A user interface initiates generation of data representing a composite display image window including data identifying a designated long term patient medical condition together with encounters and medical conditions associated with the encounters providing a user an overview of long term and short term medical conditions of a patient.

DETAILED DESCRIPTION OF THE INVENTION

Known systems partition treatment and diagnostic procedure information into records of multiple different visits of a patient with one or more healthcare provider organizations. Known systems thereby create a disjointed record which cannot be viewed in one location. In contrast, a system according to invention principles associates a clinical diagnosis with a patient, enabling treatments, diagnostic studies and clinical documentation to be stored in a patient record. The system provides a unified patient history of a diagnosis and automatically converts a financial diagnosis description of a medical condition, such as an ICD 9 code, into clinical terminology used by clinicians. The system associates a clinical diagnosis with a patient, not a visit and persists the association across multiple patient visits and not just for one visit. Further, the system associates particular processing functions with a certain diagnostic type, such as cancer and the system triggers initiation of additional necessary clinical procedures for performance by a clinician. For this purpose system 10 adds tasks to a clinician or device task list. For example, in response to a cancer diagnosis the system initiates presentation of diagnosis and disease staging dialogs to a user with appropriate security credentials.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of, hardware, firmware, and/or software.

An executable application, as used herein, comprises code or machine readable instructions for conditioning the processor to implement predetermined functions, such as those of an operating system a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition.

A Workflow Management System is a software system that manages processes. It includes a process definition function that allows users to define a process that should be followed, an Event Monitor, which captures events from a Healthcare Information System and communicates the results to the Workflow Management System. A processor in the Management System tracks which processes are running, for which patients, and what step needs to be executed next, according to a process definition. The Management System includes a procedure for notifying clinicians of a task to be performed, through their worklists (task lists) and a procedure for allocating and assigning tasks to specific users or specific teams. A document or record comprises a compilation, of data in electronic form and is the equivalent of a paper document and may comprise a single, self-contained unit of information.

Figure 1:
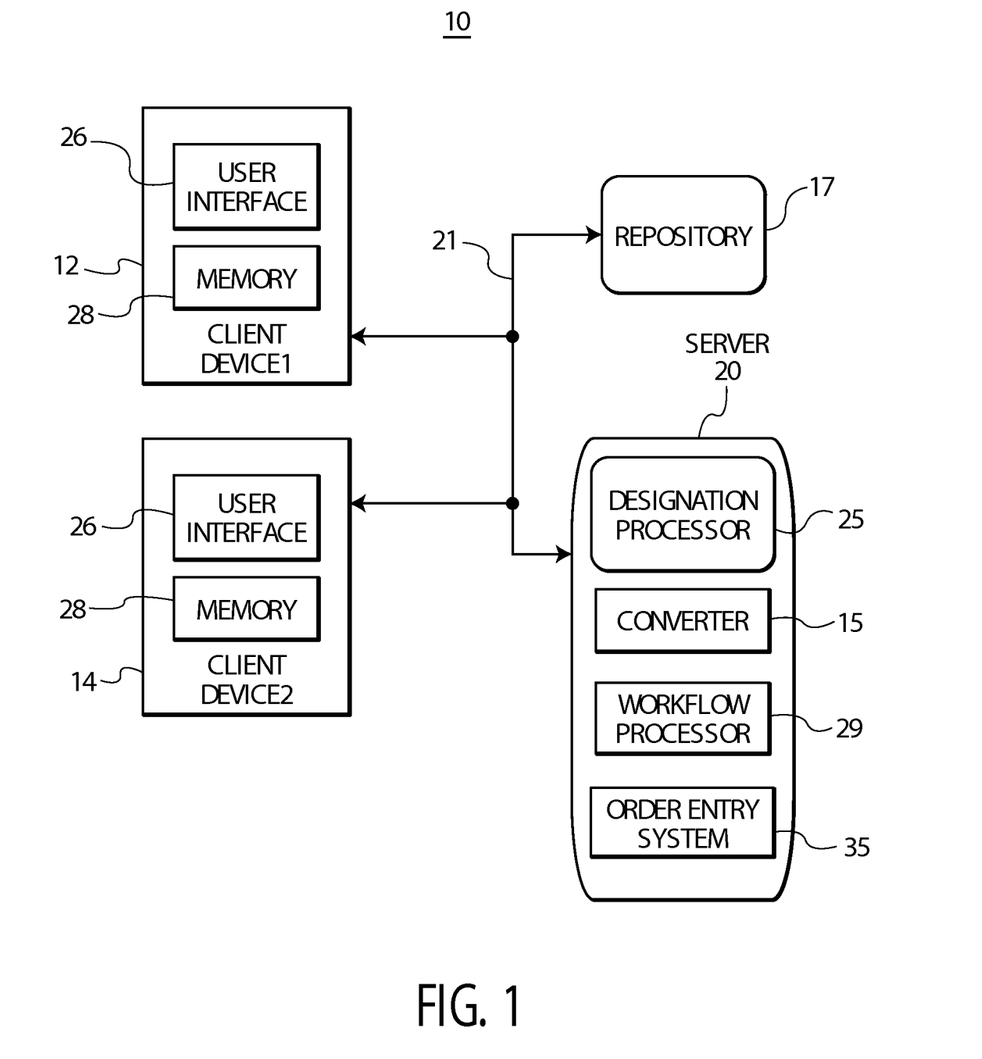
FIG. 1 shows a system for providing an overview display of patient medical condition identifying both long term and short term medical conditions, according to invention principles.

FIG. 1 shows system 10 for providing an overview display of patient medical condition identifying both long term and short term medical conditions. System 10 includes client devices (workstations) 12 and 14, repository 17 and server 20 bidirectionally communicating via network 21. Server 20 includes designation processor 25, workflow processor 29, order entry system 35 and converter 15. Designation processor 25 designates an identified patient medical condition as being long term in response to user command. At least one repository 17 stores information associating a designated long term patient medical condition with a patient and with multiple encounter identifiers identifying corresponding interactions of the patient with a healthcare provider organization and with medical conditions associated with the encounters. User interface 26 initiates generation of data representing a composite display image window including data identifying a designated long term patient medical condition together with encounters and medical conditions associated with the encounters providing a user an overview of long term and short term medical conditions of a patient. The composite display image window is presented on workstation 12 (or workstation 14).

Workflow processor 29 automatically prompts a user to confirm addition of a task to a task list of a healthcare worker in response to, designation of an identified patient medical condition as being long term and data identifying at least one of, (a) a short term medical condition of the patient, (b) an order for treatment to be administered to the patient and (c) a laboratory test result of the patient. The identified patient medical condition is identified from a condition representative code in a predetermined code set. Workflow processor 29 in server 20 manages addition, deletion and modification of tasks to be performed by a worker or device as well as presentation of task lists in a window area in a composite display image window. Converter 15 automatically translates a code representing the identified patient medical condition to a text phrase representing the identified patient medical condition (clinical diagnosis) understandable by a clinician. Converter 15 automatically translates a medical condition representative code to a text phrase using a predetermined map associating codes with one or more corresponding text phrases indicating one or more medical conditions. Converter 15 uses additional patient information including patient assessments, demographic data (e.g., age, weight, height gender), diagnosis text and other information acquired from patient records to select between different text phrases associated with a particular code.

Converter 15 converts a financial description, which is not used by clinicians (e.g., a code such as an ICD9 code), into a corresponding commonly used clinical description of a diagnosis. The clinical diagnosis is associated with a patient as well as with records associated with multiple different patient visits involved in an extended duration (e.g. a lifetime) medical condition such as diabetes, congestive heart failure, and cancer. System 10 provides a lifetime history of a clinical diagnosis and organizes clinically relevant data (diagnostics, treatment, notes) by associating the clinically relevant data with an appropriate clinical diagnosis. Thereby providing a physician with a single entry point display image window for viewing patient information. In situations in which a primary physician may not be available, this expedites a process for an attending physician to review patient history and determine a course of action, for example.

Figure 2:
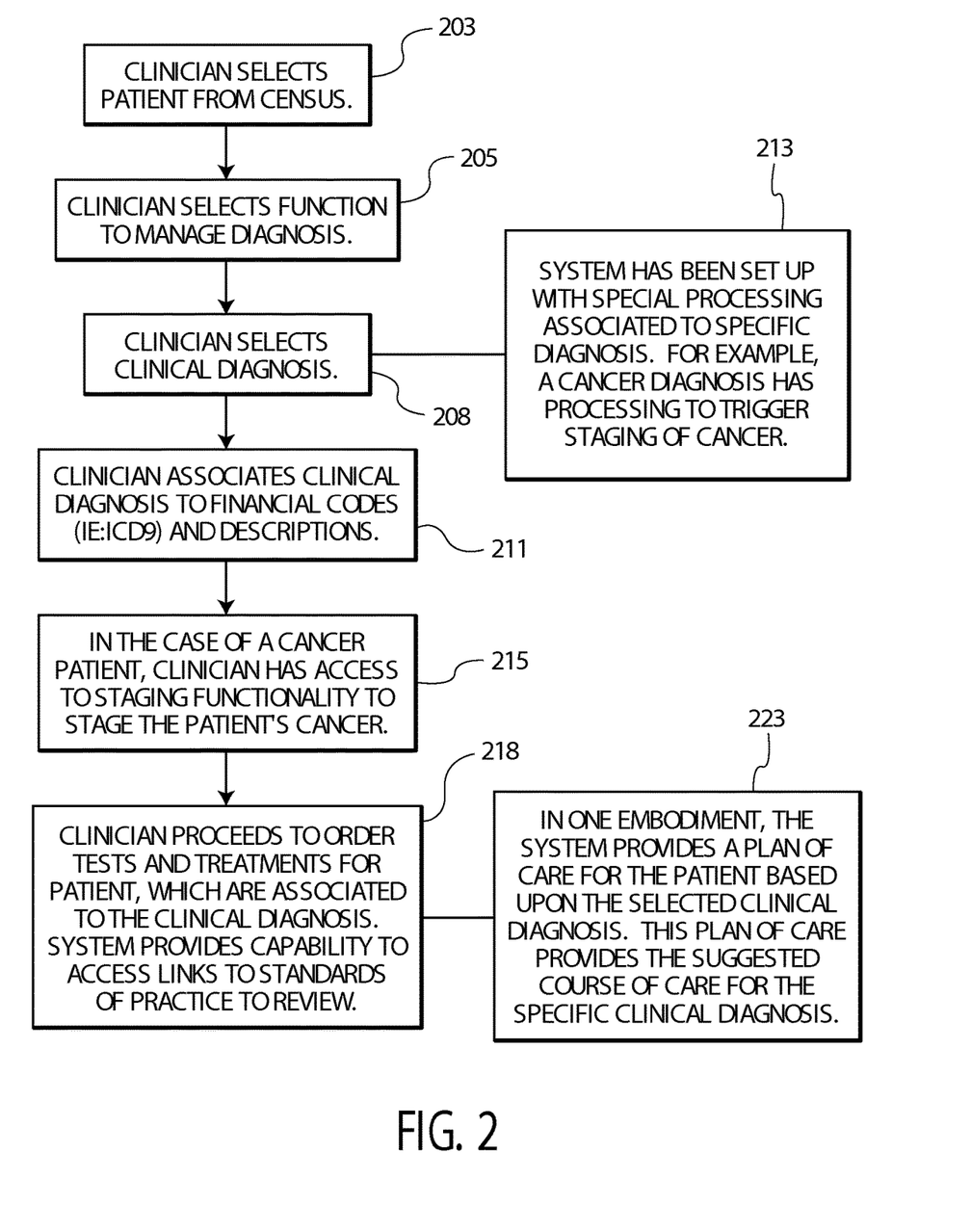
FIG. 2 shows a flowchart of a process involving providing an overview of patient medical condition and a care plan for long term and short term medical conditions, according to invention principles.
Figure 3:
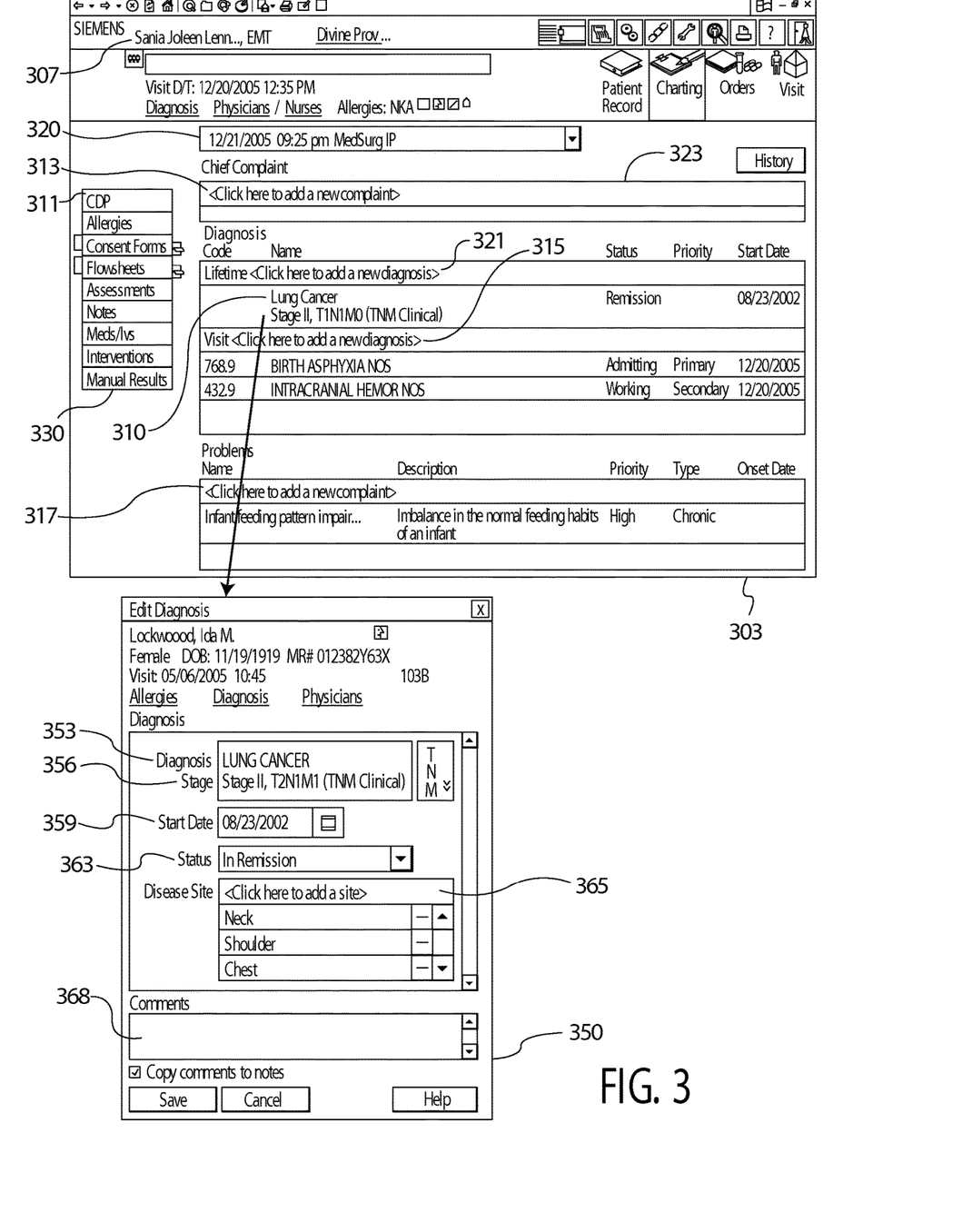
FIG. 3 shows user interface display images including data identifying a designated long term patient medical condition, encounters and medical conditions associated with the encounters as an overview of long term and short term medical conditions of a patient, according to invention principles.

FIG. 2 shows a flowchart of a process employed by system 10 in providing an overview of patient medical condition and a care plan for long term and short term medical conditions. The steps of FIG. 2 may be performed wholly or partially automatically in other embodiments. The process of FIG. 2 employs user interface display images as illustrated in FIG. 3 including data identifying a designated long term patient medical condition, encounters and medical conditions associated with the encounters providing as an overview of long term and short term medical conditions of a patient. In step 203 (FIG. 2), a user selects a particular patient from a census list of patients presented in a user interface image displayed on workstation 12 (FIG. 1) and that is associated with a particular physician, for example. In step 205 a clinician selects CDP (Clinical Data Processing) function 311 in display image 303 (FIG. 3) to initiate generation of data representing composite display image window 323 including data identifying a designated long term patient medical condition (e.g., lung cancer 310) together with encounters and medical conditions (e.g., in section 315) associated with the encounters providing a user an overview of long term and short term medical conditions of a patient. In step 213 system 10 and the FIG. 2 process are adaptively configured in response to predetermined instruction to adapt processing to a particular selected diagnosis so that data processing functions employed are adaptively selected to correspond to a particular diagnosis type. Thereby, for example, in response to a selected cancer diagnosis, system 10 prompts a user to enter staging information for use in identifying a cancer stage of a patient.

In step 208 (FIG. 2) a user selects a clinical diagnosis 310 (FIG. 3) and in step 211 associates clinical diagnosis 310 with financial (i.e., ICD9) diagnosis codes 768.9 and 432.9 in visit section 315. User interface display image 303 of FIG. 3 provides to user 307 selectable functions and associated display images indicated in column 330 including CDP (clinical data processing) 311, allergies, consent forms, flowsheets, assessments, notes, medications/IVs, interventions and manually entered patient data and results. Image window area 323 including Complaint 313, Diagnosis 321 and 315 and Problem 317 sections for Medical/surgical department 320 of a hospital is presented in response to user selection of CPD item 311. Complaint, section item 313 is selectable to initiate generation of an image menu enabling a user to enter data indicating a complaint. Diagnosis section item 315 is selectable to initiate generation of an image menu enabling a user to enter data indicating a financial reimbursement associated diagnosis code (e.g., an ICD9 code). A financial reimbursement associated diagnosis code is typically entered in individual records of each visit for use in accurate claim preparation for reimbursement of costs by a healthcare payer organization.

Diagnosis section item 321 is selectable to initiate generation of image menu 350 enabling a user to enter and associate data indicating a long term medical condition diagnosis with a financial reimbursement associated diagnosis code. The long term medical condition diagnosis is also associated with a patient and with visits in section 315 and multiple encounter identifiers identifying corresponding interactions of the patient with a healthcare provider organization and medical conditions associated with the encounters. The long term medical condition diagnosis is associated with a patient and this association persists for a time span encompassing multiple patient visits (encounters) including up to a patient lifetime for a lifetime type medical condition diagnosis. An encounter is used interchangeably with visit herein and comprises a patient interaction with a healthcare organization including an inpatient or outpatient visit, data exchange or phone call, for example.

Image menu 350 enables a user to enter and edit data indicating a clinical diagnosis 353 and corresponding stage 356 as well as an initial diagnosis date 359. The staging information is based on a user selected appropriate staging scale and source. Menu 350 also enables a user to enter and edit status 363, disease site 365 and associated comments 368. In another embodiment a short term medical diagnosis may also be entered. Problem section item 317 is selectable to initiate generation of an image menu enabling a user to enter data indicating a problem.

System 10, in step 215 (FIG. 2), adaptively configures processing in response to predetermined instruction and selected clinical diagnosis 310. Specifically, in response to selected lung cancer diagnosis 310, system 10 prompts a user to enter staging information for use in identifying a cancer stage of a patient via image menu 350. System 10 prompts a user by initiating generation of a message for communication to a user via a display image prompt, adding a task to a worker task list or by another method of communication such as by pager, phone voice message or email, for example. In an alternative embodiment, system 10 provides a user with image menu 350 without providing a prompt message. In step 218 a user initiates an order for tests or treatments to be administered to the patient. The order is associated with the selected lung cancer diagnosis 310 using order entry system 35 (FIG. 1). Order entry system 35 initiates generation of display images for presentation on workstation 12 enabling a user to place orders. The order entry display images include user selectable links (e.g., hyperlinks) enabling a user to access best practice and treatment guidelines associated with a medical condition and diagnosis. System 10 in step 223 initiates generation of a proposed plan of care based upon the selected lung cancer diagnosis 310. The proposed plan of care indicates a course of treatment for the medical condition indicated by patient diagnosis 310.

System 10 provides and stores in repository 17, a lifetime history of a clinical diagnosis. Repository 17 organizes clinically relevant data (diagnostics, treatment, notes) in association with an appropriate clinical diagnosis, providing a physician with a single entry point and display image for viewing patient information. Repository 17 associates a financial reimbursement associated diagnosis code with a clinically relevant description (e.g. ICD9 code) known and used by the clinicians. For example, ICD 9 174.9 is Malignant Neoplasm of the Breast. In the clinical world, this is translated into Breast Cancer.

Financial reimbursement associated diagnosis codes and code sets include HIPAA (Health Information Portability and Accountability Act) compatible code sets and other code sets used in a health care operation. Such code sets include, for example, ICD (International Classification of Diseases) codes, 9th Edition, Clinical Modification, (ICD-9-CM), Volumes 1, 2 and 3, as well as ICD-10 maintained and distributed by the U.S. Health and Human Services department. The code sets also include code sets compatible with HCPCS (Health Care Financing Administration Common Procedure Coding System), NDC (National Drug Codes), CPT-4 (Current Procedural Terminology), Fourth Edition CDPN (Code on Dental Procedures and Nomenclature). Further the code sets and terms include code sets compatible with SNOMED-RT "Systematicized Nomenclature of Medicine, Reference Terminology" by the College of American Pathologists, UMLS (Unified Medical Language System), by the National Library of Medicine, LOINC Logical Observation Identifiers, Names, and Codes Regenstrief Institute and the Logical Observation Identifiers Names and Codes (LOINC®) Committee, Clinical Terms also known as "Read Codes", DIN Drug Identification Numbers, Reimbursement Classifications including DRGs Diagnosis Related Groups. The code sets also include code sets compatible with CDT Current Dental Terminology, NIC (Nursing intervention codes) and Commercial Vocabulary Services (such as HealthLanguage by HealthLanguage Inc., by Apelon Inc.) and other code sets used in healthcare.

Designation processor 25 (FIG. 1) designates an identified patient medical condition as being long term, in response to user command. Designation processor 25 automatically parses data representing a patient diagnosis and identifies data indicating a potentially long term medical condition (such as cancer, diabetes or congestive heart failure) in the patient diagnosis (or data representing a patient medical condition) based on a predetermined list of potentially long term medical conditions and automatically initiates providing a user with a prompt message prompting a user to select a patient medical condition as being a long term medical condition. For this purpose designation processor 25 automatically initiates providing a user with a corresponding candidate list of potentially long term medical conditions enabling a user to select a particular long term medical condition for association with a patient. Designation processor 25 associates a designated long term patient medical condition with a particular patient. In another embodiment, designation processor 25 automatically identifies data indicating a potentially long term medical condition based on a predetermined list of potentially long term medical conditions.

In step 404 system 10 stores information in at least one repository 17 mutually associating a designated long term patient medical condition with a patient and with multiple patient visits and visit/encounter identifiers identifying corresponding interactions of the patient with a healthcare provider organization and with medical conditions associated with the encounters and with at least one financial reimbursement related diagnosis code (e.g., ICD9 code) supporting reimbursement for services provided during multiple patient visits. User interface 26 initiates generation of data representing a composite display image window including data identifying a designated long term patient medical condition and a short term patient medical condition together with multiple patient visits (encounters) and medical conditions associated with the encounters providing a user an overview of long term and short term medical conditions of a patient. The identified patient medical condition is identified from a condition representative code in a predetermined code set, for example. The composite display image window enables a user to associate at least one financial reimbursement related diagnosis code supporting reimbursement for services provided during multiple patient visits with a text phrase representing a clinical diagnosis. User interface 26 adaptively alters user interface data processing in response to a patient diagnosis. For example, a designated long term patient medical condition is cancer and user interface 26 adaptively alters user interface data processing in response to a patient diagnosis by initiating generation of data representing a display image element supporting acquisition of data identifying a stage of patient cancer from physician data entry. Further, user interface 26 also initiates generation of data representing a care plan in response to data indicating a patient diagnosis.

Workflow processor 29 automatically initiates prompting a user to confirm addition of a task to a task list of a healthcare worker in response to, designation of an identified patient medical condition as being long term and data identifying at least one of, (a) a short term medical condition of the patient, (b) an order for treatment to be administered to the patient and (c) a laboratory test result of the patient. Workflow processor 29 also adaptively alters user interface data processing in response to data indicating a patient diagnosis. Converter 15 automatically translates a code representing the identified patient medical condition (e.g., a financial reimbursement related diagnosis code) to a text phrase representing the identified patient medical condition understandable by a clinician and the composite display image window includes the text phrase. Converter 15 also automatically translates the financial reimbursement related diagnosis code to multiple text phrases representing clinical diagnoses understandable by a clinician using a predetermined map associating codes with one or more corresponding text phrases indicating one or more clinical diagnoses. Converter 15 uses additional patient information including one or more of, patient assessments, patient demographic data and patient record information, to select between different text phrases indicating one or more clinical diagnoses.

The system and processes of FIGS. 1-3 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 is usable by different healthcare facilities, departments and specialties in automatically converting a financial diagnosis description of a medical condition into clinical terminology and associating a clinical diagnosis with a patient and multiple patient visits. The processes and applications may in alternative embodiments, be located on one or more (e.g., distributed) processing devices accessing a network linking the elements of FIG. 1. Further, any of the functions and steps provided in FIGS. 1-3 may be implemented in hardware, software or a combination of both and may reside on one or more processing devices located at any location of a network linking the elements of FIG. 1 or another linked network including the Internet.

What is claimed is:

1. A computer system for performing a method for rendering a graphical user interface that dynamically displays and provides, on a computing device's display screen, a unified patient history and an overview of a medical condition of a patient by associating long term medical conditions and short term medical conditions of the patient with the patient, and persisting the association across a plurality of patient visits, the computer system comprising:

one or more computer processors;

at least one computer server;

one or more computer memory having embodied thereon computer executable instructions that when executed by the one or more processors, cause the computer system to:

identify and persistently mutually associate, a designated long term patient medical condition, the plurality of patient visits, and at least one financial reimbursement related diagnosis code supporting reimbursement for services provided during the plurality of patient visits;

store non-transitory data including the designated long term patient medical condition and the at least one financial reimbursement related diagnosis code, wherein the designated long term patient medical condition is distinguished differently from short term medical conditions in at least one repository;

convert the at least one financial reimbursement related diagnosis code to one or more clinical terminology text phrases indicating one or more clinical diagnoses corresponding to the designated long term patient medical condition, wherein the computer system uses a predetermined map associating the at least one financial reimbursement related diagnosis code with the one or more clinical terminology text phrases;

provide the graphical user interface for accessing and using the at least one repository in initiating generation of data representing a single composite display image window for providing an overview display of the designated long term patient medical condition and the short term medical conditions, separately identifying the designated long term patient medical condition and the short term medical conditions, wherein the overview display includes the one or more clinical terminology text phrases indicating the one or more clinical diagnoses; and adaptively alter user interface data processing in response to receiving data indicating that a patient diagnosis is a long term medical condition of the long term medical conditions distinct from a short term medical condition of the short term medical conditions, wherein the adaptively altering user interface data processing generates a selectable display element, on the graphical user interface, corresponding to the designated long term patient medical condition and displays the selectable display element on the single composite display image window of the graphical user interface, wherein selection of the selectable display element causes a generation and display of an image menu that enables a user to enter patient data related to the designated long term patient medical condition.

2. A computer system according to claim 1, wherein the one or more computer memory having embodied thereon computer executable instructions that when executed by the one or more processors, further cause the computer system to designate an identified patient medical condition as being long term in response to a user command.

3. A computer system according to claim 1, wherein the at least one repository stores identifiers identifying the plurality of patient visits and associating the short term medical conditions with at least one visit of the plurality of patient visits.

4. A computer system according to claim 3, wherein the single composite display image window provides a user selectable data item that enables the user to enter data representing a complaint of the patient.

5. A computer system according to claim 1, wherein the designated long term patient medical condition is at least one of: (a) cancer, (b) diabetes, and (c) congestive heart failure.

6. A computer system according to claim 1, wherein the designated long term patient medical condition is cancer and the graphical user interface adaptively alters the user interface data processing in response to a cancer diagnosis for the patient by initiating generation of data representing a display image element supporting acquisition of data identifying a stage of patient cancer from data entry from a physician.

7. A computer system according to claim 1, wherein the graphical user interface initiates generation of data representing a care plan in response to receiving the data indicating the patient diagnosis.

8. A computer system according to claim 7, wherein the one or more computer memory having embodied thereon computer executable instructions that when executed by the one or more processors, cause the computer system to automatically convert the at least one financial reimbursement related diagnosis code to a plurality of clinical terminology text phrases representing the patient diagnosis.

9. A computer system according to claim 8, wherein the computer system further uses additional patient information including at least one of: (a) patient assessments, (b) patient demographic data, and patient record information, to select between different text phrases indicating the one or more clinical diagnoses.

10. One or more computer memory having embodied thereon computer executable instructions for rendering a dynamic graphical user interface on a computing device's display screen, the graphical user interface providing a unified patient history and an overview of a medical condition of a patient by associating long term and short term medical conditions of the patient with the patient, and persisting the association across a plurality of patient visits, and provide a user with a single entry point for viewing the patient's unified patient history and overview of the patient's long term and short term medical conditions, the instructions comprising:

identifying and persistently mutually associating, a designated long term patient medical condition, with the plurality of patient visits, and at least one financial reimbursement related diagnosis code supporting reimbursement for services provided during the plurality of patient visits;

storing non-transitory data including the designated long term patient medical condition and the at least one financial reimbursement related diagnosis code, wherein the designated long term patient medical condition is distinguished differently from the short term medical conditions;

automatically converting the at least one financial reimbursement related diagnosis code to one or more text phrases indicating one or more clinical diagnoses corresponding to the designated long term patient medical condition, wherein the converting is done by using patient information from a patient record stored in at least one repository to select the one or more text phrases;

providing the graphical user interface for accessing and using the at least one repository in initiating generation of data representing a single composite display image window providing an overview display of the patient's long term and short term medical conditions, the single composite display image window separately identifying and labeling the long term and short term medical conditions, wherein the overview display includes the one or more text phrases indicating the one or more clinical diagnoses; and adaptively altering user interface data processing in response to receiving data indicating that a patient diagnosis is a long term medical condition distinct from a short term medical condition, wherein the adaptively altering user interface data processing generates a selectable display element on the graphical user interface, corresponding to the designated long term patient medical condition and displays the selectable display element on the single composite display image window of the graphical user interface, wherein selection of the selectable display element causes a generation and display of an image menu that enables the user to enter patient data related to the designated long term patient medical condition.

11. A memory according to claim 10, wherein the single composite display image window is configured to receive a user command to associate at least one financial reimbursement related diagnosis code with a text phrase representing the one or more clinical diagnosis.

\* \* \* \* \*